(12) United States Patent
Lord et al.

(10) Patent No.: US 10,717,692 B2
(45) Date of Patent: Jul. 21, 2020

(54) PROCESS FOR THE PRODUCTION OF 2-ALKYLALKANOL

(71) Applicant: JOHNSON MATTHEY DAVY TECHNOLOGIES LIMITED, London (GB)

(72) Inventors: Adrian Lord, London (GB); Martin Smidt, London (GB)

(73) Assignee: Johnson Matthey Davy Technologies Limited, London (GB)

( * ) Notice: Subject to any disclaimer, the term of this patent is extended or adjusted under 35 U.S.C. 154(b) by 0 days.

(21) Appl. No.: 16/340,830

(22) PCT Filed: Oct. 12, 2017

(86) PCT No.: PCT/GB2017/053087
§ 371 (c)(1),
(2) Date: Apr. 10, 2019

(87) PCT Pub. No.: WO2018/069714
PCT Pub. Date: Apr. 19, 2018

(65) Prior Publication Data
US 2019/0263740 A1    Aug. 29, 2019

(30) Foreign Application Priority Data

Oct. 14, 2016 (GB) .................... 1617463.3

(51) Int. Cl.
*C07C 29/17* (2006.01)
*C07C 29/36* (2006.01)
(Continued)

(52) U.S. Cl.
CPC ............ *C07C 29/17* (2013.01); *C07C 29/141* (2013.01); *C07C 29/36* (2013.01); *C07C 29/38* (2013.01);
(Continued)

(58) Field of Classification Search
CPC ......... C07C 29/17; C07C 29/36; C07C 29/80; C07C 29/175; C07C 45/66; C07C 45/73
See application file for complete search history.

(56) References Cited

U.S. PATENT DOCUMENTS 4,138,588 A * 2/1979 Tummes ............... C07C 29/141
568/881
4,684,750 A    8/1987 Kessen et al.
(Continued)

FOREIGN PATENT DOCUMENTS

GB    1252678 A    11/1971
GB    1362071 A    7/1974

OTHER PUBLICATIONS

GB1617463.3, Search Report Under Section 17(5) dated Aug. 21, 2017.
(Continued)

*Primary Examiner* — Yate' K Cutliff
(74) *Attorney, Agent, or Firm* — BakerHostetler

(57) ABSTRACT

A process for the production of 2-alkylalkanol from an aldehyde is disclosed. The process comprises the steps of: feeding aldehyde to a reactor (42) operated under condensation and dehydration conditions such that reaction occurs and an unsaturated aldehyde is produced; recovering a stream from the reactor (42) comprising the unsaturated aldehyde and feeding said stream to a first hydrogenation reactor (45) operated under conditions such that at least some of the unsaturated aldehyde is converted to 2-alkylalkanol; recovering the stream from the first hydrogenation reactor (45) comprising the 2-alkylalkanol, one or more of unreacted acrolein, alkylalkenol and alkylalkanal and heavies; passing the stream recovered from the first hydrogenation reactor (45) to a first distillation zone (48) where at least some of the heavies are separated from the stream; recovering a stream from the first distillation zone (48) compris-
(Continued)

Figure 1:
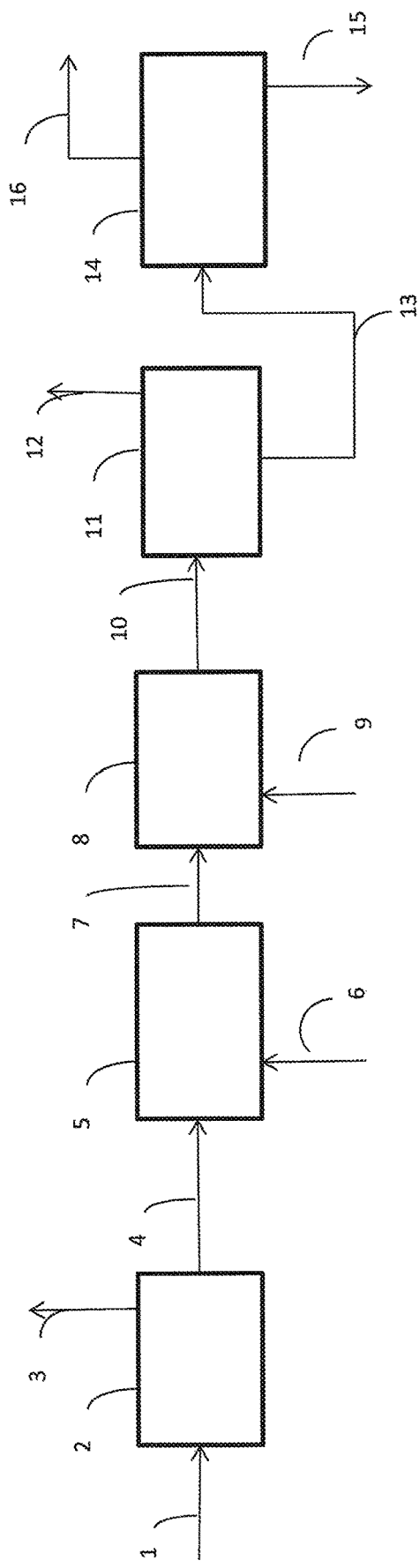

ing the 2-alkylalkanol, one or more of unreacted acrolein, alkylalkenol and alkylalkanal, said stream having a reduced heavies content when compared to the stream fed to the first distillation zone (48), and feeding said stream to a second hydrogenation reactor (51) operated under conditions such that at least one of the unreacted acrolein, alkylalkenol and alkylalkanal are converted to 2-alkylalkanol; and recovering a stream from the second hydrogenation reactor (51) comprising an increased 2-alkylalkanol content compared to the stream fed to the second hydrogenation reactor (51).

14 Claims, 3 Drawing Sheets

(51) Int. Cl.
| | | |
|---|---|---|
| *C07C 29/80* | (2006.01) | |
| *C07C 31/125* | (2006.01) | |
| *C07C 45/73* | (2006.01) | |
| *C07C 29/38* | (2006.01) | |
| *C07C 29/141* | (2006.01) | |
| *C07C 45/66* | (2006.01) | |

(52) U.S. Cl.
CPC ............ *C07C 29/80* (2013.01); *C07C 31/125* (2013.01); *C07C 45/66* (2013.01); *C07C 45/73* (2013.01)

(56) References Cited

U.S. PATENT DOCUMENTS

| | | | |
|---|---|---|---|
| 5,227,544 A * | 7/1993 | Thurman | C07C 29/141 568/491 |
| 5,434,313 A | 7/1995 | Harrison et al. | |
| 6,340,787 B1 | 1/2002 | Simeray et al. | |
| 7,663,006 B2 * | 2/2010 | Oota | C07C 29/141 568/881 |
| 9,006,495 B2 | 4/2015 | Krokoszinski et al. | |
| 2004/0092780 A1 | 5/2004 | Zgorzelski et al. | |
| 2008/0242899 A1 | 10/2008 | Oota et al. | |
| 2012/0253083 A1 * | 10/2012 | Kaizik | C07C 29/175 568/881 |

OTHER PUBLICATIONS

GB1716736.2 Combined Search and Examination Report Under Sections 17 and 18(3) dated Jun. 22, 2018.
PCT/GB2017/053087 International Search Report dated Jan. 23, 2018.
PCT/GB2017/053087 lWritten Opinion, dated Jan. 23, 2018.

* cited by examiner

PROCESS FOR THE PRODUCTION OF 2-ALKYLALKANOL

CROSS-REFERENCE TO RELATED APPLICATIONS

This application is the National Stage of International Patent Application No. PCT/GB2017/053087, filed Oct. 12, 2017, which claims priority to Great Britain Patent Application No. 1617463.3, filed Oct. 14, 2016, the entire disclosures of both of which applications are incorporated herein by reference for any and all purposes.

FIELD

The present invention relates to a process for the production of 2-alkylalkanols. More particularly it relates to the production of 2-alkylalkanols by the condensation of two aldehyde molecules. Still more particularly it relates to the production of 2-ethylhexanol from nbutyraldehyde or the production of 2-propylheptanol from n-valeraldehyde.

BACKGROUND 2-ethylhexanol is produced industrially on a large scale. To manufacture the 2-ethylhexanol, two molecules of n-butyraldehyde undergo aldol condensation and dehydration to give 2-ethylhexenal which is also known as ethylpropylacrolein. This is then subjected to hydrogenation to provide crude 2-ethylhexanol. Generally the hydrogenation reaction does not go to completion and the crude product will not only contain unreacted 2-ethylhexenal but may also contain one or both of 2-ethylhexenol and 2-ethylhexanal i.e. the compounds in which only one of the unsaturated group and the carboxyl group has been hydrogenated.

Since the desired 2-ethylhexanol is mainly used to make esters such as dioctyl phthalate which serve as plasticizers in the production of polyvinyl chloride, it is necessary to produce the 2-ethylhexanol with a high level of purity.

One measure of the purity is the colour of the product or rather the absence of colour in the product. An indication of the desired level of purity is that the product not only has low intrinsic colour, it must also produce a low colour in a standard test after being boiled with sulphuric acid. One such test is set out in BS 4583. In this test the sample is treated with concentrated sulphuric acid under conditions specified in the Standard. Any impurities in the sample form coloured compounds by reactions which are catalysed by the sulphuric acid. Once the sample has been reacted with the sulphuric acid, the colour is compared with that of a series of platinum cobalt standards of equal volume in matched 100 ml Nessler tubes. These standards are also known as APHA or Hazen standards. The APHA standard relates to the US standard ASTM D1209. By the use of this test an accelerated determination is provided of any undesirable colour which may be produced when the 2-ethylhexanol is reacted with acids such as phthalic acid to produce esters.

It is the presence of unreacted 2-ethylhexenal, and any partially hydrogenated 2-ethylhexenol and/or 2-ethylhexanal which cause the undesirable results and the sulphuric acid test will identify their presence.

Similar issues are noted with the production of other 2-alkylalkanols such as the production of 2-propylheptanol from n-valeraldehyde where the product comprises unreacted valeraldhyde and partial hydrogenation products. The n-valeraldehyde starting material will generally comprise up to about 10% of other C5 aldehydes. Where these are present, the product will comprise these other C5 aldehydes.

A conventional process for the production of 2-alkylalkanols such as 2-ethylhexanol or 2-propylheptanol is illustrated schematically in FIG. 1. In this process the starting aldehyde is passed in line 1 to reactor 2 where an aldol condensation reaction is carried out to form an unsaturated aldehyde, i.e. an acrolein. The by-product water, which is generally separated by decantation, is removed in line 3. The acrolein is then passed in line 4 to a hydrogenation reactor 5 to which hydrogen is added in line 6. The hydrogenation may be carried out in the liquid or vapour phase. A catalyst, such as one containing one or more Group VI-X metals such as copper, chromium, nickel, zinc, iridium or ruthenium, will generally be used. Suitable hydrogenation catalysts will generally include those available from Johnson Matthey as the Pricat and HTC range.

The product stream recovered from the hydrogenation reactor 5 comprising some alkylalkanol is recovered in line 7. This stream will generally also comprise small quantities of unsaturated alcohol and saturated aldehyde. Some unreacted unsaturated aldehyde may also be present. The stream is therefore passed to a polishing hydrogenation zone 8 where it is contacted with hydrogen supplied in line 9 to further hydrogenate the unsaturated alcohol and saturated aldehyde. Catalyst will generally also be used for the polishing hydrogenation.

A product stream is recovered from the polishing hydrogenation reactor 8 in line 10 and is then subjected to a two stage distillation process. In a first distillation zone 11, lights are removed in line 12. A stream having a reduced lights concentration is then passed in line 13 to a second distillation zone 14 where the heavies are separated and removed in line 15. The product stream of alkylalkanol is recovered in line 16.

Various modifications of the hydrogenation and purification sequences have been suggested with a view to improving the quality of the product, improving catalyst life or both improving the quality of the product and improving catalyst life.

DE 1003702 describes a process in which a low pressure hydrogenation reaction is carried out. This leaves from 4 and 15% aldehyde unconverted. The product of this first hydrogenation reaction may optionally be subjected to distillation to remove light compounds such as 2-ethylhexanal. The product of the first hydrogenation from which at least some light compounds have been removed is then subjected to a high pressure hydrogenation to remove the lights and heavies. Whilst the acid colour of the product is not specifically described, it is described that the carbonyl number is 0.1 and it can therefore be inferred that the acid colour will be above 60.

An alternative arrangement is described in GB1252678. In this arrangement, the product of the aldolisation is subjected to distillation to remove heavies before it is passed to the hydrogenation reaction.

A further process is illustrated in U.S. Pat. No. 7,663,006. Here there is a suggestion that dihydropyrans are acid colour making by-products. It is further commented that it is difficult to separate these dihydropyrans from 2-ethylhexenal by distillation and it is therefore proposed that their presence in the purification step should be limited. In one arrangement it is suggested that this is achieved by distillation of the feed to the hydrogenation reactor to remove heavies or a two stage hydrogenation reactor using different catalysts. The process described in U.S. Pat. No. 7,663,006 is illustrated schematically in FIG. 2.

In this process the starting aldehyde is passed in line 21 to reactor 22 where an aldol condensation reaction is carried out to form an unsaturated aldehyde, i.e. an acrolein. The by-product water is separated by decantation and removed in line 23. The acrolein is then passed in line 24 to a first distillation zone 25 where heavies are separated and removed in line 26. The stream of the unsaturated aldehyde having a reduced heavies content is passed in line 27 to hydrogenation reactor 28 to which hydrogen is added in line 29. The product stream recovered from the hydrogenation reactor 29 is recovered in line 30. This stream will comprise some alkylalkanol and will generally also comprise small quantities of unsaturated alcohol and saturated aldehyde. Some unreacted unsaturated aldehyde may also be present. This stream is then passed to a polishing hydrogenation reactor 31 where it is contacted with hydrogen supplied in line 32 to further hydrogenate any unreacted unsaturated aldehyde and the unsaturated alcohol and saturated aldehyde.

A product stream is recovered from the polishing hydrogenation reactor 31 in line 33 and is then subjected to a two stage distillation process. In a second distillation zone 34, lights are separated and removed in line 35. A stream having a reduced lights concentration is then passed in line 36 to a third distillation zone 37 where the heavies are separated and removed in line 38. The product stream is recovered in line 39.

Whilst this process may assist in the removal of colour forming compounds, the requirement for a distillation zone between the aldolisation reactor and the hydrogenation reactor together with the requirement for two reaction zones after the polishing hydrogenation reactor adds to the capital and operating costs of the process.

In addition, carrying out distillation on the stream comprising the unsaturated aldehyde, which is generally a vacuum distillation, is disadvantageous since air leakage can occur which can cause the formation of acids and aldehydes which are known to produce heavy compounds from condensation reactions when heated.

It is therefore desirable to provide a process which enables 2-alkylalkanols to be produced with a low acid colour and with a minimum number of processing steps to reduce capital and operating costs. It is also desirable that at least some of the other problems noted with prior art processes are at least partially overcome and preferably obviated.

SUMMARY

It has now been found that a product having an acceptable purity as measured by acid colour can be achieved using a simplified hydrogenation and refining process in which the product from the aldolisation reaction is passed to hydrogenation without being subjected to prior distillation and then subjecting the product of the first hydrogenation reactor to distillation to remove heavies before the product is subjected to the polishing hydrogenation reaction. It has surprisingly been found that with this arrangement, not only can the desired product be achieved at the required level of purity, a two stage distillation process after the polishing hydrogenation may be avoided such that only lights removal is required.

Thus according to the present invention there is provided a process for the production of 2-alkylalkanol from an aldehyde comprising the steps of:

(a) feeding aldehyde to a reactor operated under condensation and dehydration conditions such that reaction occurs and an unsaturated aldehyde is produced;
(b) recovering a stream from the reactor of step (a) comprising the unsaturated aldehyde and feeding said stream to a first hydrogenation reactor operated under conditions such that at least some of the unsaturated aldehyde is converted to 2-alkylalkanol;
(c) recovering the stream from the first hydrogenation reactor comprising the 2-alkylalkanol, one or more of unreacted acrolein, alkylalkenol and alkylalkanal and heavies;
(d) passing the stream recovered in step (c) from the first hydrogenation reactor to a first distillation zone where at least some of the heavies are separated from the stream;
(e) recovering a stream from the first distillation zone comprising the 2-alkylalkanol, one or more of unreacted acrolein, alkylalkenol and alkylalkanal, said stream having a reduced heavies content when compared to the stream fed to the first distillation zone, and feeding said stream to a second hydrogenation reactor operated under conditions such that at least one of the unreacted acrolein, alkylalkenol and alkylalkanal are converted to 2-alkylalkanol; and
(f) recovering a stream from the second hydrogenation reactor comprising an increased 2-alkylalkanol content compared to the stream fed to the second hydrogenation reactor.

Optionally, the stream recovered from the second hydrogenation reactor in step (f) may be passed to a second distillation zone where lights are removed.

DRAWINGS

FIG. 1 represents a schematic representation of one conventional prior art process.

Figure 2:
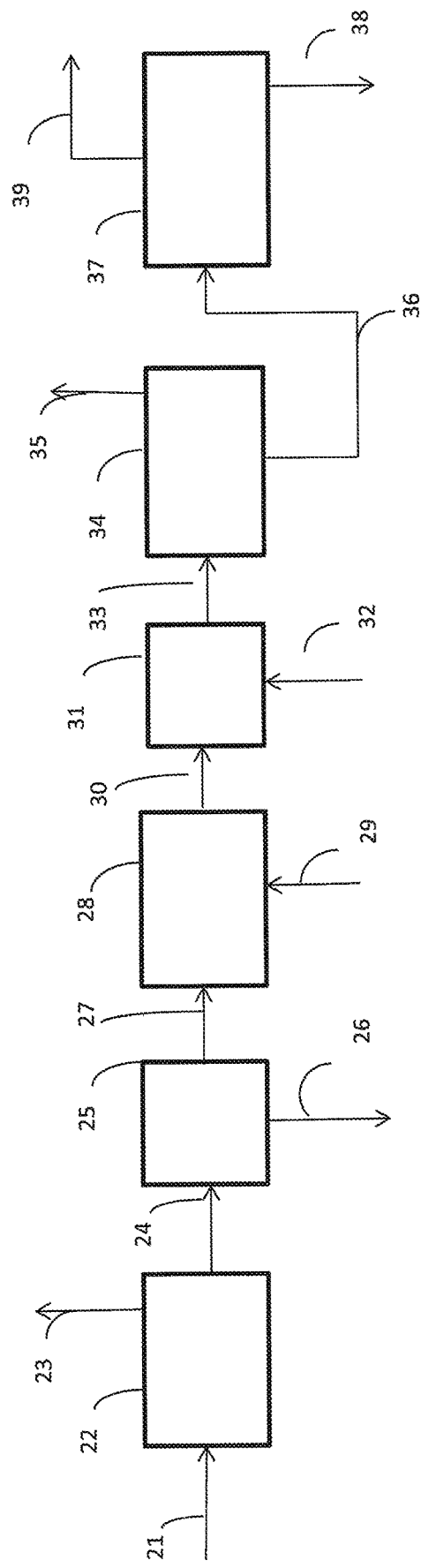

FIG. 2 is a schematic representation of the prior art process as described in U.S. Pat. No. 7,663,006.

Figure 3:
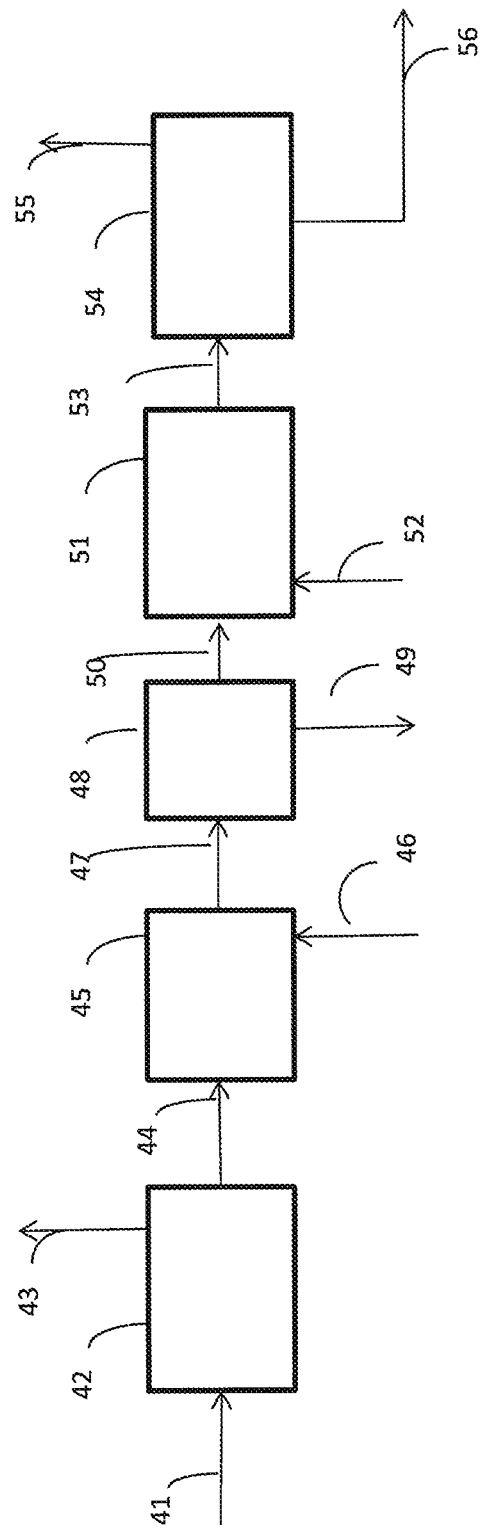

FIG. 3 provides a schematic representation of the process according to the present disclosure.

DETAILED DESCRIPTION

It has been surprisingly been found that the removal of heavies between the first hydrogen reactor and the second hydrogenation reactor obviates the need for heavy removal after the second hydrogenation reactor and so unlike the arrangement in U.S. Pat. No. 7,663,006 there is no increase in the number of distillation zones required. Thus the process of the present invention does not include a heavies removal after the stream has been treated in the second hydrogenation reactor.

It will be understood that 'heavies' are components which have a higher boiling point than the 2-alkylalkanol and the 'lights' are components which have a lower boiling point than the 2-alkylalkanol.

The process of the present invention may be used for the preparation of any 2-alkylalkanol from an aldehyde. In one arrangement, the aldehyde will have at least 3 carbon atoms. In one arrangement, it may have from 3 to 10 carbon atoms. The aldehyde may be straight chain or branched. The process of the present invention is particularly suitable for use in the production of 2-ethylhexanol from n-butyraldehyde or the production of 2-propylheptanol from n-valeraldehyde.

It will be understood that the aldehyde used in the present invention may comprise minor amounts of hydrocarbons and/or heavy by-products from the reaction in which the aldehyde is formed. Generally, the aldehyde will have been formed in a hydroformylation reaction and so the heavy by-products may be those formed in hydroformylation. Generally these hydrocarbons and/or heavy by-products will be present in amounts of less than about 0.5%. Other aldehydes may also be present in the feed. For example where the feed to the process of the present invention is n-butyraldehyde, 2-methylpropionaldehyde may be present. Similarly where the feed is n-valeraldehyde, 2-methylbutyraldehyde and 3-methylbutyraldehyde may be present.

The reactor in which condensation and dehydration occurs such that the aldehyde is converted to the unsaturated aldehyde may be of any suitable configuration. It will be understood that the condensation is an aldol reaction. The reaction may be carried out by any method.

Examples of suitable methods can be found in U.S. Pat. Nos. 5,434,313, 6,340,778 and 9,006,495, which are incorporated herein by reference. In general, the aldehyde is reacted at about 80° C. to about 100° C. A catalyst may be present. In one arrangement sodium hydroxide may be used as the catalyst. This may be present in a 1 to 5 wt % aqueous solution.

The liquid reaction mixture is generally separated into an aqueous phase comprising the aqueous alkali solution which will include the water of reaction. This phase may be removed by any suitable means. Generally it is removed by decantation. At least some of the aqueous phase may be recycled to the reactor to provide the catalyst. It may be concentrated before it is recycled.

The oily phase from the reactor, which will comprise unsaturated aldehyde, is passed to the first hydrogenation reactor. In this reactor the majority of the unsaturated aldehyde is hydrogenated. This will therefore generally be known as a 'bulk hydrogenation'.

The first hydrogenation reactor may be operated under any suitable conditions. A catalyst will generally be used. Any suitable catalyst may be used. Generally the active component of the catalyst will be based on metals from Groups VI to X. Suitable examples include copper, nickel, manganese, zinc, cobalt, palladium, ruthenium and iron. The catalyst may be supported. Any suitable support may be used. Suitable supports include alumina, silica or diatomaceous earth. A particularly suitable catalyst may be a supported copper chromite catalyst. The catalyst may also include a promoter to enhance selectivity. Any suitable promoter may be used. Barium may be a suitable promoter.

The hydrogenation in the first hydrogenation reactor may be carried out in the liquid or vapour phase. Any suitable configuration may be used and the reactor may be operated under any suitable conditions. Whilst the particular conditions selected will depend on the catalyst chosen, the hydrogenation in the first hydrogenation reactor may be carried out at a temperature of from about 100° C. to about 200° C. and at a pressure of from atmospheric to about 15 MPa.

Where a liquid phase hydrogenation is to be used, it may be performed in any suitable manner. In one arrangement it may be carried out as downflow over packed beds of catalyst. A large recycle of cooled product may be mixed with the feed in order to remove the heat of reaction. One example of a suitable process is described in GB1362071 which is incorporated herein by reference. In an alternative arrangement one or more heat exchangers may be used to remove the heat of reaction.

Where a nickel catalyst is used in a liquid phase reaction, the temperature may be below about 150° C. at a pressure of from about 10 to about 30 bara. Where a copper chromite catalyst is used in a liquid phase reaction the temperature may be from about 100° C. to about 150° C. or from about 100° C., to about 200° C., at a pressure of from about 15 to about 30 bara.

Where a gas phase hydrogenation is to be used, it may be performed in any suitable manner. A typical gas phase hydrogenation which may be used is that described in Hydrocarbon Processing, March 1983, pages 67 to 74, which is incorporated herein by reference.

Where a nickel catalyst is used in a gas phase reaction, the temperature may be from about 100° C. to about 150° C. at a pressure of from atmospheric to about 5 bara. Where a copper chromite catalyst is used in a gas phase reaction the temperature may be from about 135° C. to about 170° C. at a pressure of from atmospheric to about 5 bara.

In this bulk hydrogenation the majority of the unsaturated aldehyde will be hydrogenated.

The majority of the unsaturated aldehyde will be converted to the desired 2-alkylalkanol. However, some products of partial hydrogenation will also be formed. Thus one or both of alkylalkenol and alkylalkanal may be formed. Heavies will also be generated during the hydrogenation.

The product from the first hydrogenation reactor is then passed to the first distillation zone for heavies removal. Any suitable means may be used provided that it enables heavies removal. The distillation in the first distillation zone may be carried out by any suitable means. In one arrangement, it may be conducted using a refluxed distillation column having from about 20 to about 50 theoretical stages. In one arrangement, the column may include sieve or valve trays. In one another arrangement, a structured packing may be used. The distillation may be carried out at any suitable conditions. In one arrangement the column top pressure will be in the region of from about 0.05 bara to about 0.5 bara. The bottoms temperature will generally be kept below about 175° C.

Once the heavies have been removed, the stream is passed to the second hydrogenation reactor. As the majority of the unsaturated aldehyde will have been hydrogenated in the first hydrogenation reactor this second hydrogenation will generally be directed to completing any partial hydrogenation. Of course, where there is any unhydrogenated unsaturated aldehyde remaining in the feed to the second hydrogenation reactor this will be subjected to hydrogenation. The reactor, conditions and/or the catalyst used in the second hydrogenation reactor may be the same or different to those used in the first hydrogenation reactor. However, generally the second hydrogenation will carried out in the liquid phase. This may be carried out over a packed bed of catalyst. The flow over the catalyst bed may be upflow or downflow. Any suitable catalyst may be used. In one arrangement, the active component of the catalyst may be nickel. Palladium or ruthenium may also be used as active components. The catalyst may be supported. Any suitable support may be used. Suitable supports include alumina, silica or diatomaceous earth. A promotor may be used. Generally it will not be necessary to recycle cooled product to mix with the feed to order to remove the heat of reaction. The hydrogenation may be carried out at any suitable conditions. In one arrangement, the second hydrogenation may be carried out at a temperature of from about 80° C. to about 150° C. and at a pressure of from about 10 to about 35 bara.

The product stream from the second hydrogenation reactor will have a higher content of the desired 2-alkylalkanol than that fed to it.

This product stream is then fed to a second distillation zone where lights are removed. Any suitable means may be used provided that it enables lights removal. The distillation carried out in the second distillation zone may be carried out by any suitable means. The means may be the same or different to that used in the first distillation zone. In one arrangement, it may be conducted using a refluxed distillation column having from about 20 to about 50 theoretical stages. In one arrangement, the column may include sieve or valve trays. In one another arrangement, a structured packing may be used. The distillation may be carried out at any suitable conditions. In one arrangement the column top pressure will be in the region of from about 0.05 bara to about 0.5 bara. The bottoms temperature will generally be kept below about 175° C.

The product recovered from at or near the bottom of the second distillation zone will have an increased content of 2-alkyl alkanol of the feed to the distillation zone. In one arrangement, the stream will have more than 98%, more than 99%, or more than 99.5% 2-alkyl alkanol.

The present invention will now be described by way of example with reference to the accompanying drawings in which:

FIG. 1 is a schematic representation of one conventional prior art process;

FIG. 2 is a schematic representation of the prior art process as described in U.S. Pat. No. 7,663,006; and FIG. 3 is a schematic representation of the process according to the present invention.

It will be understood by those skilled in the art that the drawings are diagrammatic and that further items of equipment such as reflux drums, pumps, vacuum pumps, temperature sensors, pressure sensors, pressure relief valves, control valves, flow controllers, level controllers, holding tanks, storage tanks, and the like may be required in a commercial plant. The provision of such ancillary items of equipment forms no part of the present invention and is in accordance with conventional chemical engineering practice.

The present invention will be described with reference to the production of 2-ethylhexanol from n-butyraldehyde. However, it will be understood that it is equally applicable to the production of other 2-alkylaldehydes including the production of 2-propylheptanol from n-valeraldehyde.

As illustrated in FIG. 3, the n-butyraldehyde is fed in line 41 to a reactor 42 which is operated such that an aldol condensation and dehydration reaction occurs to form the unsaturated aldehyde acrolein. The water produced is removed in line 43. The product stream from the reactor is passed inline 44 to the first hydrogenation reactor 45 where it is reacted with hydrogen that is supplied in line 46. In this hydrogenation reactor 45 the bulk of the unsaturated aldehyde is converted to the desired 2-ethylhexanol. There will also be some partial hydrogenation such that one or both of 2-ethylhexenol and 2-ethylhexanal are formed.

This stream is then passed in line 47 to the first distillation zone 48 which is operated to remove heavies which may have been formed. These heavies are removed in line 49. The stream from which the heavies have been removed is then passed in line 50 to the second hydrogenation reactor 51. In this polishing reactor 51 the stream is contacted with hydrogen added in line 52. In general this polishing reactor 51 will enable the 2-ethylhexenol and 2-ethylhexanal to be converted to the desired 2-ethylhexanol thereby improving the purity of the product.

The product stream from the second hydrogenation zone 51 is optionally passed in line 53 to a second distillation zone 54 where lights such as heptane are separated and removed in line 55. The product 2-ethylhexanol is then recovered in line 56. This product will have an acid colour below 20 APHA.

The present invention will now be described with reference to the accompanying examples.

Preparation of Standards

The standards used to determine the acid colour in the examples of the present invention were prepared according to BS4583. Potassium chloroplatinate stock solution of normal 500 APHA is prepared by dissolving 1.245 g of potassium chloroplatinate, $K_2PtCl_6$ and 1.000 g of cobaltous chloride, $CoCl_2.6H_2O$ in distilled water. 100 ml of hydrochloric acid is added and the mixture diluted to 1 litre with distilled water, in a volumetric flask. Platinum cobalt reference standards, in 100 ml Nessler tubes, are prepared by diluting this 500 APHA stock solution so that for example diluting 1 ml of stock to 100 ml produces a reference colour of 5 APHA.

Testing of Samples

Once product is obtained, it is boiled with sulphuric acid and the sample colour compared with the reference colours. 8 ml of the concentrated sulphuric acid (Aristar) is added dropwise to 100 ml of the sample in a 250 ml wide mouthed conical flask. The contents of the flask are stirred constantly during the addition of the acid, using a magnetic stirrer and follower. The mixture is heated for a period of 60±1 minute in a boiling water-bath maintained at 99 to 100° C. The flask is removed from the bath and immediately placed in cold water to cool the contents rapidly to room temperature.

100 ml of the sample is introduced into a Nessler tube after any required filtering. In a colour comparator the tube colour is matched with one of the previously prepared standards. The number of the colour standard which most nearly matches the sample is then reported. Where the colour of the sample lies between two standards, the darker of the two is used.

Example 1

98% 2-ethylhexanol made by caustic catalysed aldolisation of n-butyraldehyde was dried below 1000 ppm water using a molecular sieve. This was pumped and passed downflow over chrome-free copper catalyst bed for 1620 hours at an average LHSV 0.5 $hr^{-1}$ bed at an inlet/outlet temperature of 165° C. and 180° C. respectively at a hydrogen pressure of 28 bara. The bed temperature was controlled by recycling cooled product from outlet of the bed to the reactor inlet. Outlet 2-ethylhexaldehyde concentration was 0.15 wt %.

The product was distilled to remove heavy compounds to less than 0.02 wt % at 0.3 bara with a reboiler temperature of 165° C. This is then polished over nickel catalyst at 85° C. and a flow rate of LHSV 3 $hr^{-1}$. Since there was less than 0.02 wt % heavies in the stream from the second hydrogenation further distillation to remove heavies was not required. Without distillation to remove lights the product was on-specification for acid colour. The APHA colour was <5 and the sulphuric acid colour was <5. Acidity as acetic acid was ≤0.005 wt % and the carbonyl as ethylhexanal was ≤0.01 wt % and the iodine value was ≤0.01 g/100 g.

Example 2

Example 1 was repeated except that the first hydrogenation reactor was carried out using a copper/chrome catalyst. The product from the first hydrogenation reactor was distilled to remove heavy compounds and then polished in the second hydrogenation reactor over nickel catalyst at 85° C., LHSV 3 hr$^{-1}$, 28.5 bara hydrogen pressure using 0-5% excess hydrogen. Without distillation to remove lights the product was on-specification for acid colour. The sulphuric acid colour was ≤5. Carbonyl as ethylhexanal was ≤0.015 wt % and the iodine value was 0.015 g/100 g.

Example 3

Crude propylbutyl acrolein comprising 0.1 wt % C5 aldehyde, 0.4 wt % lights and 4.9 wt % propylbutylacrolein isomers was prepared by aldolisation of mixed C5 aldehyde fed at LHSV of 1.7 hr$^{-1}$ downflow to a packed bed of copper catalyst. Hydrogen was supplied to maintain a pressure of 29 bara. Product was recycled at 13:1 aldehyde:feed rate from the reactor base to the feed point at the reactor top to control reactor temperature inlet and outlet to 150° C. to 175° C. The hydrogenation product was distilled to remove heavies at 0.1 bara with reflux/feed ratio of 0.5 and bottoms temperature 160° C. The column overheads were polished at 112° C. downflow LHSV 3.2 hr$^{-1}$ over a nickel catalyst at 20 bara. The sulphuric acid colour was >5 and <10 before lights removal. After lights removal the heavy impurities were below 0.02 wt % so that no distillation to remove heavies was required.

Example 4

Crude propylbutyl acrolein comprising 0.3 wt % C5 aldehyde, 0.1 wt % lights, 4.9 wt % propylbutylacrolein isomers and 1.1 wt % heavies, was prepared by aldolisation of mixed C5 aldehydes and fed at LHSV of 0.5 hr$^{-1}$ downflow to a packed bed of chrome-free copper catalyst. Hydrogen was supplied to maintain a pressure of 19 bara. Cooled product was recycled from the reactor base to the feed point at the reactor top to control reactor inlet and outlet temperatures of 140° C. and 165° C. The product was subjected to hydrogenation. The hydrogenation product was distilled to remove heavies at 0.1 bara top pressure with reflux/feed ratio of 0.5 and a bottoms temperature of 160° C. Polishing hydrogenation was performed downflow over chrome-free copper catalyst at LHSV of 1.0 hr$^{-1}$, 140 to 145° C. and 19 bara hydrogen pressure. The acid colour was 15 and the heavies make in the product was <0.05 wt %.

Comparative Example 1

Example 4 was repeated. However, the distillation to remove heavies was not carried out before the polishing hydrogenation but was instead carried out after it. It had an acid colour of 25 to 30.

It can therefore be seen that carrying out the heavies removal between the bulk and polishing hydrogenation significantly improves the quality of the obtained product.

The invention claimed is:

1. A process for the production of 2-alkylalkanol from an aldehyde comprising the steps of:
    (a) feeding aldehyde to a reactor operated under condensation and dehydration conditions such that reaction occurs and an unsaturated aldehyde is produced;
    (b) recovering a stream from the reactor of step (a) comprising the unsaturated aldehyde and feeding said stream to a first hydrogenation reactor operated under conditions such that at least some of the unsaturated aldehyde is converted to 2-alkylalkanol;
    (c) recovering the stream from the first hydrogenation reactor comprising the 2-alkylalkanol, one or more of unreacted acrolein, alkylalkenol and alkylalkanal and heavies;
    (d) passing the stream recovered in step (c) from the first hydrogenation reactor to a first distillation zone where at least some of the heavies are separated from the stream;
    (e) recovering a stream from the first distillation zone comprising the 2-alkylalkanol, one or more of unreacted acrolein, alkylalkenol and alkylalkanal, said stream having a reduced heavies content when compared to the stream fed to the first distillation zone, and feeding said stream to a second hydrogenation reactor operated under conditions such that at least one of the unreacted acrolein, alkylalkenol and alkylalkanal are converted to 2-alkylalkanol; and
    (f) recovering a stream from the second hydrogenation reactor comprising an increased 2-alkylalkanol content compared to the stream fed to the second hydrogenation reactor.

2. The process according to claim 1 where the stream recovered from the second hydrogenation reactor in step (f) is passed to a second distillation zone where lights are removed, said second distillation zone having no heavies removal.

3. The process according to claim 1 wherein the aldehyde is n-butyraldehyde and the product is 2-ethylhexanol.

4. The process according to claim 1 wherein the aldehyde is n-valeraldehyde and the product is 2-propylheptanol.

5. The process according to claim 1 wherein the first hydrogenation reactor is operated at a temperature of from about 100° C. to about 200° C. and at a pressure of from atmospheric pressure to about 15 MPa.

6. The process according to claim 1 wherein a nickel catalyst is used in the first hydrogenation reactor.

7. The process according to claim 6 wherein the first hydrogenation reactor is operated at a temperature of about 150° C. or below and a pressure of from about 10 to about 30 bara where the reaction is carried out in the liquid phase or at a temperature of from about 100° C. to about 150° C. and a pressure of from atmospheric to about 5 bara where the reaction is carried out in the gas phase.

8. The process according to claim 5 wherein a copper catalyst is used in the first hydrogenation reactor.

9. The process according to claim 8 wherein the first hydrogenation reactor is operated at a temperature of from about 100° C. to about 150° C. and a pressure of from about 15 to about 30 bara where the reaction is carried out in the liquid phase or at a temperature of from about 135° C. to about 170° C. and a pressure of from atmospheric to about 5 bara where the reaction is carried out in the gas phase.

10. The process according to claim 1 wherein the second hydrogenation reactor is operated in the liquid phase.

11. The process according to claim 10 wherein the second hydrogenation reactor is operated at a temperature of from about 80° C. to about 150° C. and at a pressure of from about 10 bara to about 35 bara.

12. The process according to claim 1 wherein the bottoms temperature in the first and second distillation zone is below about 175° C.

13. The process according to claim 1 wherein the pressure at a top of the first distillation zone is in the region of from about 0.05 bara to about 0.5 bara.

14. The process according to claim 2 wherein the pressure at a top of the second distillation zone is in the region of from about 0.1 bara to about 0.8 bara.

* * * * *